United States Patent [19]

Shiber

[11] Patent Number: 4,732,154
[45] Date of Patent: Mar. 22, 1988

[54] ROTARY CATHETER SYSTEM
[75] Inventor: Samuel Shiber, Mundelein, Ill.
[73] Assignee: Surgical Systems & Instruments, Inc., Mundelein, Ill.
[21] Appl. No.: 874,546
[22] Filed: Jun. 16, 1986

Related U.S. Application Data

[63] Continuation-in-part of Ser. No. 609,846, May 14, 1984, abandoned.

[51] Int. Cl.$^4$ .............................................. A61B 17/32
[52] U.S. Cl. ................................................... 128/305
[58] Field of Search .................. 128/305, 305.1, 310, 128/304, 751–758, 344, 348.1; 604/22

[56] References Cited

U.S. PATENT DOCUMENTS

| | | | |
|---|---|---|---|
| 1,596,754 | 8/1926 | Moschelle | 604/282 |
| 2,505,358 | 4/1950 | Gusberg et al. | 128/751 |
| 3,614,953 | 10/1971 | Moss | 128/305.1 |
| 4,030,503 | 6/1977 | Clark | 128/356 X |
| 4,177,797 | 12/1979 | Baylis et al. | 128/754 |
| 4,249,541 | 2/1981 | Pratt | 128/753 |
| 4,445,509 | 5/1984 | Auth | 128/305 |
| 4,479,497 | 10/1984 | Fogarty et al. | 728/344 |
| 4,589,412 | 5/1986 | Kensey | 128/305 |
| 4,627,436 | 12/1986 | Leckrone | 128/303.1 |

FOREIGN PATENT DOCUMENTS

| | | | |
|---|---|---|---|
| 2804015 | 8/1979 | Fed. Rep. of Germany | 128/305 |
| 2044103 | 10/1980 | United Kingdom | 128/754 |
| 665908 | 6/1979 | U.S.S.R. | 128/304 |

Primary Examiner—Michael H. Thaler
Attorney, Agent, or Firm—Samuel Shiber

[57] ABSTRACT

A rotary catheter system insertable into a patient's artery over a non rotating auger shaped guide-wire for remotely cutting and removing an obstruction therein, having a flexible catheter equipped with a tubular-blade at its front end and a motor connected to its other end.

9 Claims, 8 Drawing Figures

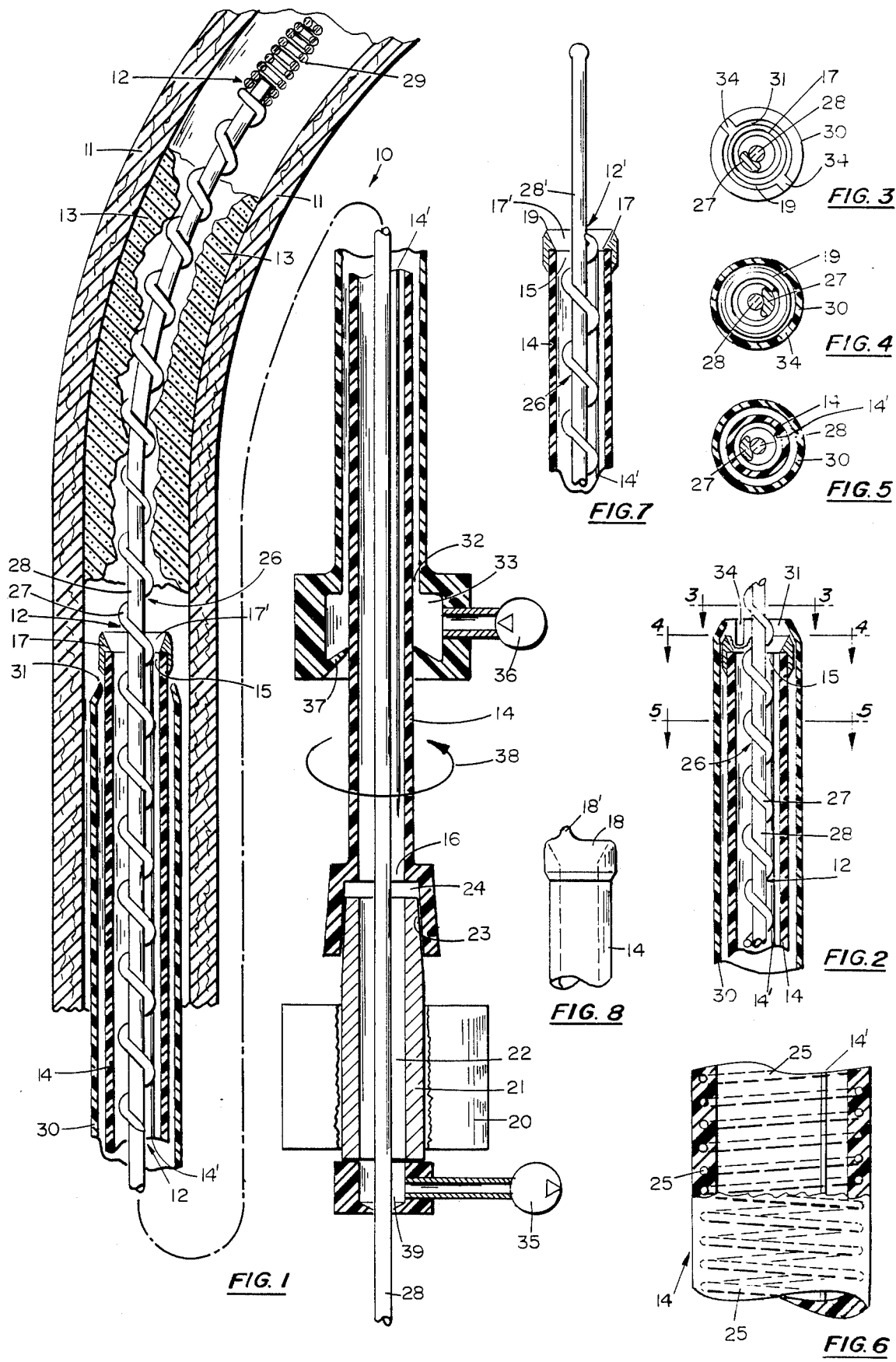

ROTARY CATHETER SYSTEM

This application is a continuation-in-part of application Ser. No. 609,846 which was filed on May 14, 1984 now abandoned, which is hereby being incorporated by reference.

BACKGROUND AND OBJECTIVE OF THE INVENTION

With age a large portion of the population develops arterial obstructions formed by fats, fibrous material and calcified deposits, resulting in a diminished blood circulation. Presently such obstructions are circumvented surgically by providing a bypass or they are treated with a catheter equipped with a balloon which is inserted into the obstruction through the arterial system and then inflated to expand the obstruction's lumen. A problem with this treatment is that it may burst the artery and in certain cases it is ineffective. Further, it does not remove the obstruction material out of the arterial system.

The objective of the present invention is to provide a catheter rotatable over a guide-wire, equipped with a tubular-blade attached to its front end, that would cut and extract the obstruction material. The rotary catheter system should be producable in diameters down to 1-2 millimeters (mm) and a length of up to a meter to be able to reach and enter small and remote arteries. Preferably, the operation of the rotary catheter system would resemble the operation of present catheters as much as possible so present skills of medical personnel can be utilized. This and other objectives of the invention will become apparent from the following discussion and the accompanying drawings.

BRIEF DESCRIPTION OF THE FIGURES

FIG. 1 shows a general cross sectional view of a rotary catheter system inserted into an obstructed artery. The central portion of the rotary catheter system is represented by a phantom line due to space limitations on the drawing sheet.

FIG. 2 shows a front end area of the rotary catheter system with a tubular-blade retracted in a sleeve.

FIG. 3 shows a cross sectional view of the rotary catheter system along a line 3—3 marked on FIG. 2.

FIG. 4 shows a cross sectional view of the rotary catheter system along a line 4—4 marked on FIG. 2.

FIG. 5 shows a cross sectional view of the rotary catheter system along a line 5—5 marked on FIG. 2.

FIG. 6 shows a cross sectional view of an enlarged portion of a reinforced flexible catheter.

FIG. 7 shows an optional guide-wire.

FIG. 8 shows an optional tubular-blade.

DETAILED DESCRIPTION OF THE DRAWINGS

FIG. 1 generally shows a rotary catheter system 10 insertable into a patient's artery 11 over a guide-wire 12 (similar parts are identified with same numbers throughout the FIGS.) for remotely cutting and removing an obstruction 13. The rotary catheter system 10 has:

A flexible-catheter 14 having a front end 15 and a rear end 16, being rotatable around the guide-wire 12.

A tubular-blade 17 mounted to the front end 15. The term tubular-blade, as used herein, means a blade which cuts a narrow circular pass on a periphery of the obstruction 13 separating the center core of the obstruction. The tubular-blade 17 has a through hole 17' in its center for ingesting the obstruction material and passing it into the flexible-catheter 14. A tubular-blade is much more efficient in ingesting the obstruction material and it requires less energy input than other blades which pulverize all of the obstruction material. To illustrate this point, when the tubular-blade 17 extracts an obstruction with an outisde diameter of 3 mm, an inside diameter (lumen) of 1 mm and a length of 10 mm, the area that the tubular-blade 17 has to cut through is approximately 100 square mm. If a conventional blade, for example as shown in U.S. Pat. No. 4,445,509 by Auth, is used to break the same obstruction to shavings measuring 0.1 m by 0.1 mm by 0.5 mm the area that the conventional blade would have had to cut through is 2700 square mm, and this larger area requires a substantially larger energy input to the blade. The tubular-blade 17 is sharpened along a circular line 19 as shown in FIGS. 3 and 7. FIG. 8 shows an optional tubular-blade 18 having a sharp protruding fingre 18' which similarly cuts the obstruction along a narrow peripheral path.

A motor 20 has a shaft 21 with a drilled through hole 22 and a tapered end 23 which is connected to a matching tapered seat 24 formed integral with the rear end 16. The motor rotates the flexible-catheter 14 and the tubular-blade 17 in the direction shown by arrow 38. The flexible-catheter 14 is preferably made of plastic material and a reinforcing wire 25.

At least a portion of the length of the guide-wire 12 which is located near the front end 15 is shaped as an auger 26. Preferably, the guide-wire 12 is formed, as shown in FIGS. 1 and 2, by a spaced spiral-wire 27 attached to the core-wire 28. The sprial-wire 27 extends beyond the core-wire 28 to form a soft spring 29 which can be gently pushed through the artery 11 and the obstruction's lumen. The auger 26 is of sufficient length so that during operation a section of it (several centimeters) is inside the flexible-catheter 14 to assure accurate guidance of the flexible-catheter 14 on the guide-wire 12 and a positive mechanical conveying of obstruction material into the flexible-catheter 14. The rest of the guide-wire 12 can be made of the core-wire 28 alone to minimize friction between the guide-wire 12 and the flexible-catheter 14. An optional guide-wire 12' shown in FIG. 7 has a bare core-wire 28' extending forward of the auger for entering an obstruction with an extremely narrow lumen. An optional small ridge 14' is formed integral with the flexible-catheter 14 on its inner wall to assure the rotation of the obstruction material inside the flexible-catheter 14. The ridge 14' starts at the vicinity of the first end 15 and longitudinally extends along the auger 26.

Preferably, the flexible-catheter 14 is rotatably disposed in a sleeve 30 having a front opening 31 and a rear opening 32. When the rotary catheter system 10 is inserted into the artery 11 the flexible-catheter 14 and tubular-blade 17 are kept retracted in the sleeve 30 as shown in FIG. 2, to prevent injury to the artery 11. The rear end 16 extends outwardly from the rear opening 32. Upon reaching the obstruction's site, the rear opening 32, which is formed integral with a rotary fluid joint 33, is held in place and the flexible-catheter 14 is pushed to slide in the sleeve 30 and push the tubular-blade 17 through the front opening 31 of the sleeve 30, as shown in FIG. 1. The front opening 31 is smaller in diameter than the tubular-blade 17, but it contains two slits 34 which make it flexible enough to allow the tubular-blade 17 to pass through.

Suction means 35 are connected to the rear end 16, through the hole 22 and a rotary fluid joint 39, to assist in pulling obstruction material into and through the flexible-catheter 14, however, care should be given to the level of negative pressure created in the artery 11 not to collapse it and thereby draw it towards the tubular-blade 17.

Means for introducing fluid 36 to the vicinity of the tubular-blade 17 are connected to the rear opening 32 through the rotary fluid joint 33 which has an integral seal 37. The rotary fluid joint 33 directs the fluid into the sleeve 30 around the flexible-catheter 14 and does not interfere with the rotation of the flexible-catheter 14 in the sleeve 30.

It can be appreciated that the torque generated by the motor 20 is partially dissipated by frictional losses along the rotating flexible-catheter 14, therefore, the flexible-catheter can be manufactured with a variable cross section, i.e., a larger diameter and/or wall thickness at the vicinity of the rear end 16 than in the vicinity of the front end 15. The cross sectional change can be gradual or in steps. This gives the flexible-catheter 14 the required increased torque carrying capacity in the vicinity of its rear end. This refinement of design is useful, for example, when treating small arteries of the heart where entry into the body is often at the groin area requiring a long catheter, and the obstruction may be located in an artery requiring the front end of the flexible-catheter to have a diameter of around 1 mm. Since the arteries that are used as a corridor for reaching the heart are of larger diameter there is usually no problem in accommodating the larger diameters away from the front end of the flexible catheter.

It can be noted in general, that the rotary catheter system can be manufactured in different diameters and lengths depending on the size and site of artery that it is intended for. It can be appreciated that the smaller the diameter that the catheter can be manufactured to, the smaller the artery that it can enter. By making the guide-wire also function as an auger, and by driving the tubular blade through the tube of the catheter compactness is achieved allowing the rotary catheter system to be made to enter obstructed arteries in the heart and brain which have a lumen of around 1 mm.

OPERATION

A process for removing the obstruction 13 from an artery 11 comprises the following steps:

Inserting into the artery 11 the guide-wire 12 and the flexible-catheter 14 with the tubular-blade 17, preferably disposed in the sleeve 30, to a vicinity of the obstruction 13 in the artery 11.

Placing the front portion of the guide-wire 12 in the obstructed area as shown in FIG. 1. This is a common procedure for inserting catheters and should not pose special problems. The guide-wire 12 can be manually manipulated and turned so that the spiral-wire 27 screws itself or otherwise works its way into the obstruction 13. The soft spring 29 minimizes the danger of perforating the arterial wall. The soft spring 29 can be bent in cases that the guide-wire 12 has to be inserted to an arterial branch, again in line with present practice.

Once the guide-wire 12 is in place, the flexible-catheter 14 and the tubular-blade 17 are advanced through the front opening 31 and continue to be advanced while being rotated over the guide-wire 12. At the same time, the guide-wire 12 and the sleeve 30 are prevented from being rotated by the flexible-catheter 14. As the tubular-blade 17 cuts the obstruction 13 it ingests it and leads it into the flexible-catheter 14. As the obstruction material enters the tubular-blade 17 and the flexible-catheter 14 it contacts their inner walls and the small ridge 14' and starts rotating around the auger 26 which pushes the rotating obstruction material deeper into the tube making room for additional obstruction material to be ingested. Finally, the rotary catheter system 10 containing the obstruction material is withdrawn out of the artery 11.

During the cutting, the front end 15 and tubular-blade 17 are accurately guided by the guide-wire 12 since the outside diameter of the guide-wire 12 is, preferably, close to the inside diameter of the flexible-catheter 14. The accurate guidance of the tubular-blade 17 reduces its chances of cutting the arterial wall, espcecially when cutting along a curved artery 11 as illustrated in FIG. 1. It can be seen that a solid wire of the same diameter as the auger 26 would prevent, rather than assist, the obstruction material from entering the flexible-catheter 14. A thin wire, such as core wire 28 by itself, would not provide accurate guidance nor would it provide positive conveying of obstruction material into the flexible-catheter 14.

Fluid can be delivered to the obstruction site through the sleeve 30, around the flexible-catheter 14. Such fluid can lubricate the rotation of the flexible-catheter 14 in the sleeve 30, irrigate the cutting site and act as a flushing medium of obstruction particles into the flexible-catheter 14, especially in conjunction with suction applied to the flexible-catheter 14. The fluid may be radio-opaque to assist x-raying the process. Alternatively, prior to cutting, fluid can also be delivered through the flexible-catheter 14.

Diameter and length of the rotary-catheter 10 components may vary in relation to the size and location, respectively, of the artery that they are intended for. The sequence of insertion of the components into the artery may depend on the nature and the location of the obstruction, for example, in clearing an artery of a leg the guide-wire 12 may be inserted first followed by the sleeve 30 and flexible-catheter 14. When clearing arteries of a heart the sleeve 30 containing the flexible-catheter 14 may be first inserted to the vicinity of the obstruction then the guide-wire 12 may be placed in position followed by the operation as discussed above. Alternatively, a standard guiding catheter may be inserted first to assist in properly placing the guide-wire 12 in the obstruction site, than the standard guiding catheter is withdrawn while the guide-wire 12 remains in place and then the rotary catheter system 10 can be slid over the guide-wire 12 to the obstruction site.

While the present invention has been illustrated by single embodiment, it should be understood that various modifications and substitutions may be made without departing from the spirit of the invention or the scope of the claims.

I claim:

1. A rotary catheter system insertable into a patient's artery for remotely cutting and removing an obstruction therein, comprising in combination:
   a flexible guide-wire insertable into a patient's artery, at least a portion of said flexible guide-wire being shaped as an auger,
   a rotary flexible-catheter with front and rear ends, said flexible-catheter being rotatably disposed and slidable over said flexible guide-wire, a tubular-blade mounted to said front end, said tubular-blade having a through hole communicating with said flexible-catheter for passing obstruction material through said hole and into said flexible-catheter, means connected to said rear end for rotating said flexible-catheter and said tubular-blade around said flexible guide-wire.

2. A rotary catheter system as in claim 1, wherein a small longitudinal ridge is formed on at least a portion of an inner wall of said flexible-catheter.

3. A rotary catheter system as in claim 1, wherein said flexible-catheter has a larger diameter in the vicinity of said rear end than in the vicinity of said front end.

4. A rotary catheter system as in claim 1, wherein said flexible-catheter has a higher torque carrying capacity in the vicinity of said rear end than in the vicinity of said front end.

5. A rotary catheter system as in claim 1, wherein suction means are connected to said flexible catheter.

6. A rotary catheter system as in claim 1, having sleeve with a front opening and a rear opening, said flexible-catheter being rotatably disposed in said sleeve.

7. A rotary catheter system as in claim 6, said sleeve is longitudinally slidable over said flexible-catheter.

8. A rotary catheter system as in claim 7, said front opening is smaller in diameter than said tubular-blade to ease penetration of said rotary catheter system into the artery.

9. A rotary catheter system as in claim 7, wherein means for introducing fluids to the vicinity of said tubular-blade are connected to said sleeve.

* * * * *